(12) United States Patent
Archer et al.

(10) Patent No.: US 9,908,891 B2
(45) Date of Patent: Mar. 6, 2018

(54) PROCESS FOR THE PREPARATION OF MORPHINAN-6-ONE COMPOUNDS

(71) Applicant: JOHNSON MATTHEY PUBLIC LIMITED COMPANY, London (GB)

(72) Inventors: Nicolas Archer, Edinburgh (GB); Timothy Davies, Edinburgh (GB); Amy Price, Edinburgh (GB); Maureen Young, Edinburgh (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/909,573

(22) PCT Filed: Feb. 5, 2014

(86) PCT No.: PCT/GB2014/050324
§ 371 (c)(1),
(2) Date: Feb. 2, 2016

(87) PCT Pub. No.: WO2015/015147
PCT Pub. Date: Feb. 5, 2015

(65) Prior Publication Data
US 2016/0176887 A1    Jun. 23, 2016

(30) Foreign Application Priority Data
Aug. 2, 2013   (GB) .................................. 1313915.9

(51) Int. Cl.
*C07D 489/08*   (2006.01)
*C07D 489/02*   (2006.01)

(52) U.S. Cl.
CPC .................. *C07D 489/08* (2013.01)

(58) Field of Classification Search
CPC ............................ C07D 489/02; C07D 489/08
USPC ...................................................... 546/45, 44
See application file for complete search history.

(56) References Cited

U.S. PATENT DOCUMENTS

| | | | |
|---|---|---|---|
| 4,272,541 A | 6/1981 | Kotick et al. | |
| 4,861,921 A | 8/1989 | Fellmann et al. | |
| 7,129,248 B2 * | 10/2006 | Chapman | C07D 489/02 514/282 |
| 8,703,950 B2 * | 4/2014 | Keskeny | C07D 489/08 546/44 |
| 8,871,779 B2 * | 10/2014 | Buehler | C07D 489/08 514/282 |
| 8,916,707 B2 * | 12/2014 | Archer | C07D 489/08 546/44 |
| 9,120,800 B2 * | 9/2015 | Grant | C07D 489/08 |
| 2008/0206883 A1 | 8/2008 | Black | |
| 2009/0270624 A1 | 10/2009 | Weigl et al. | |
| 2013/0102784 A1 | 4/2013 | Reisch et al. | |

FOREIGN PATENT DOCUMENTS

| | | |
|---|---|---|
| CN | 101115757 A | 1/2008 |
| CN | 101652371 A | 2/2010 |
| CN | 102946870 A | 2/2013 |
| DE | 2205225 | 8/1973 |
| DE | 37 08 851 A1 | 9/1987 |
| WO | WO2006084389 A1 | 8/2006 |
| WO | 2008/070656 A2 | 6/2008 |
| WO | 2008/072018 A1 | 6/2008 |
| WO | 2008072018 | 6/2008 |
| WO | 2008/118654 A1 | 10/2008 |
| WO | 2008118654 | 10/2008 |
| WO | 2011/032214 A1 | 3/2011 |
| WO | WO2011032214 A1 | 3/2011 |
| WO | 2011/141488 A2 | 11/2011 |
| WO | WO2013188418 A1 | 12/2013 |

OTHER PUBLICATIONS

International Search Report PCT/GB2014/050324 dated Apr. 4, 2014.
Findlay et al: "The Acid-catalyzed Conversion of Codeinone to 8-Hydroxydihydrocodeinone", Journal of the American Chemical Society, vol. 73, No. 8, 1965, pp. 4001-4004.
GB1401963.2, Search Report Under Section 17, dated Sep. 30, 2014.

\* cited by examiner

*Primary Examiner* — Charanjit Aulakh

(74) *Attorney, Agent, or Firm* — Baker & Hostetler LLP

(57) ABSTRACT

The present invention provides processes for preparing morphinan-6-one compounds, in particular oxymorphone and salts thereof, having improved impurity profiles.

26 Claims, 2 Drawing Sheets

PROCESS FOR THE PREPARATION OF MORPHINAN-6-ONE COMPOUNDS

Figure 1:
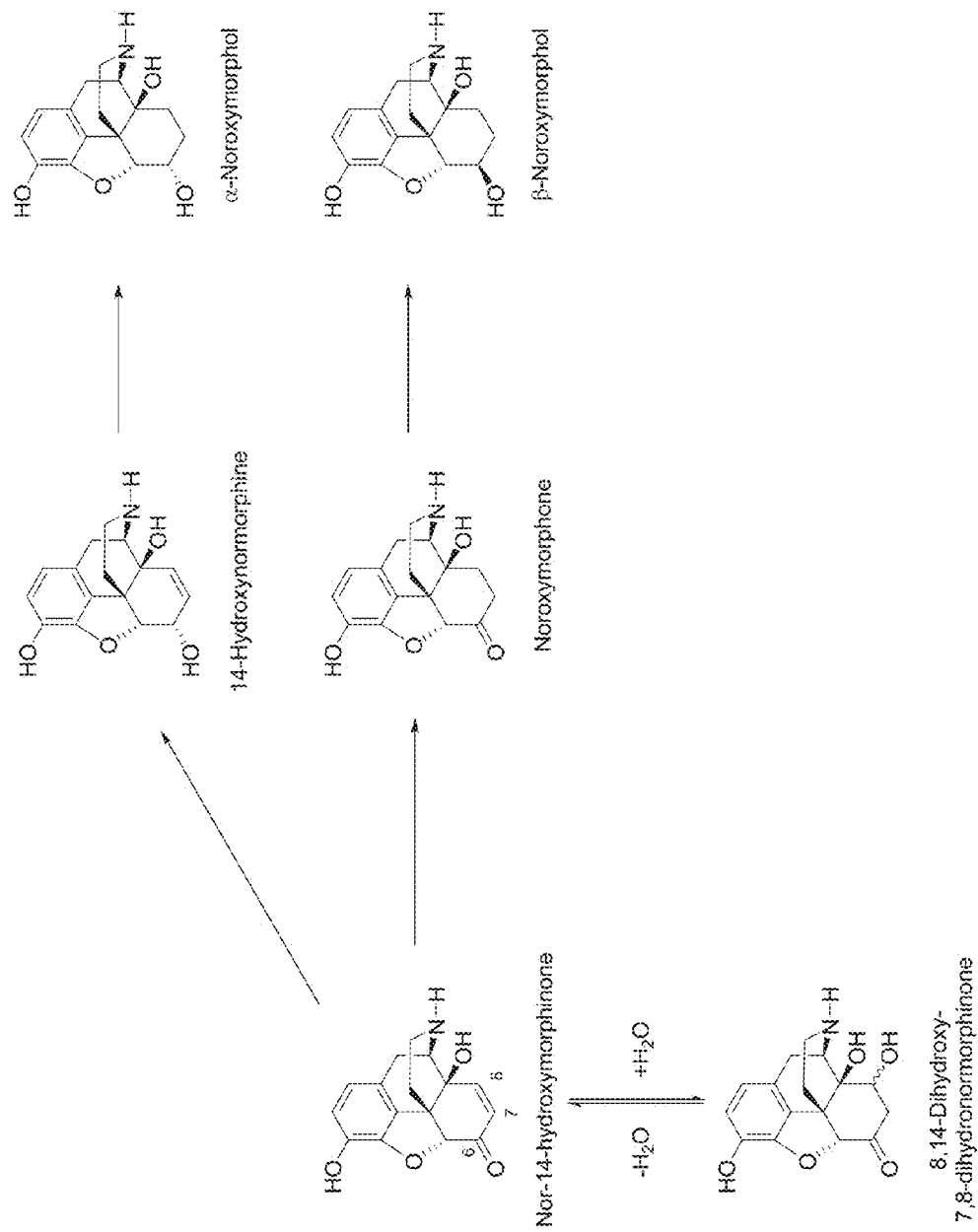

The present invention concerns processes for the synthesis of morphinan-6-one compounds, in particular noroxymorphone and salts thereof, having improved impurity profiles.

Findlay et al (Journal of the American Chemical Society, 1951, 73, 4001) describes the acid-catalyzed conversion of codeinone to 8-hydroxydihydrocodeinone.

A recent concern in the pharmaceuticals industry has been to prepare Active Pharmaceutical Ingredients (APIs) which are free or substantially free of potentially genotoxic impurities (PGIs). Compounds which contain an α,β-unsaturated ketone moiety have been identified as potential genotoxins which need to be controlled. Routes to semi-synthetic opiate alkaloid APIs often involve intermediate compounds which contain an α,β-unsaturated ketone (ABUK). As intermediates, these compounds have no therapeutic benefit and, it has been argued, their presence in APIs as impurities increases the level of risk to a patient. As such, there has been much interest in reducing the level of ABUKs in APIs as far as possible.

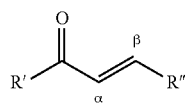

We have developed improved processes which overcome the disadvantages associated with prior art methods. The present processes are suitable for the large-scale or industrial manufacture of morphinan-6-one compounds, such as noroxymorphone and salts thereof.

In a first aspect, therefore, the invention provides a process for preparing a compound of formula (3), the process comprising the steps of:
(a) providing an aqueous acidic solution comprising a compound of formula (1) and, as an impurity, a compound of formula (2); and
(b) treating the aqueous acidic solution of step (a) such that the compound of formula (2) dehydrates to form a compound of formula (1) and the compound of formula (1) is reduced to form an aqueous acidic solution of the compound of formula (3),

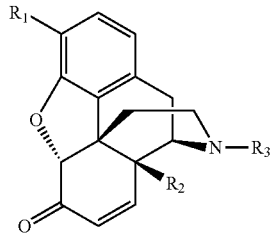

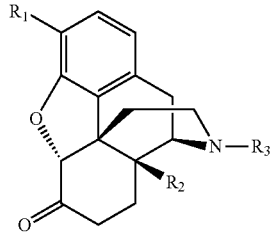

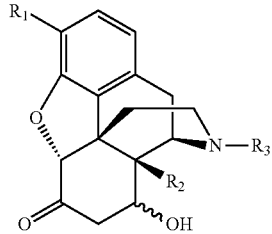

wherein:
the treating of step (b) is carried out at one or more temperatures greater than ambient in the presence of a hydrogenation catalyst and hydrogen gas; and
wherein for the compounds of formulae (1), (2) and (3):
  i) $R_1$ is —OH, $R_2$ is —OH and $R_3$—H; or
  ii) $R_1$ is —OCH$_3$, $R_2$ is —H and $R_3$—CH$_3$; or
  iii) $R_1$ is —OH, $R_2$ is —H and $R_3$—CH$_3$; or
  iv) $R_1$ is —OCH$_3$, $R_2$ is —H and $R_3$—H; or
  v) $R_1$ is —OH, $R_2$ is —H and $R_3$—H; or
  vi) $R_1$ is —OCH$_3$, $R_2$ is —OH and $R_3$—H.

In one preferred embodiment, $R_1$ is —OH, $R_2$ is —OH and $R_3$—H for the compounds (1), (2) and (3).

The chemical names for the compounds (1), (2) and (3) are set out below:

|  | $R_1$ | $R_2$ | $R_3$ | Compound (1) | Compound (2) | Compound (3) |
|---|---|---|---|---|---|---|
| i) | —OH | —OH | —H | Nor-14-hydroxymorphinone | 8,14-Dihydroxy-7,8-dihydronormorphinone | Noroxymorphone |
| ii) | —OCH$_3$ | —H | —CH$_3$ | Codeinone | 8-Hydroxy-7,8-dihydrocodeinone | Hydrocodone |
| iii) | —OH | —H | —CH$_3$ | Morphinone | 8-Hydroxy-7,8-dihydromorphinone | Hydromorphone |
| iv) | —OCH$_3$ | —H | —H | Norcodeinone | 8-Hydroxy-7,8-dihydronorcodeinone | Norhydrocodone |
| v) | —OH | —H | —H | Normorphinone | 8-Hydroxy-7,8-dihydronormorphinone | Norhydromorphone |
| vi) | —OCH$_3$ | —OH | —H | Nor-14-hydroxycodeinone | 8,14-Dihydroxy-7,8-dihydronorcodeinone | Noroxycodone |

In step (a), the process comprises providing an aqueous acidic solution comprising a compound of formula (1) and, as an impurity, a compound of formula (2).

The compounds of formula (1) may be prepared by known methods. For example, nor-14-hydroxymorphinone and nor-14-hydroxycodeinone may be prepared by the methods described in WO2005/028483 (to GlaxoSmithKline Australia Pty Ltd and Johnson Matthey PLC) starting from oripavine and thebaine respectively.

The compound (2) is an impurity. By "impurity" we mean a compound which is undesirably present and typically occurs in small quantities. The impurity may be present in the starting material, produced during the course of the reaction and/or is present in the product. Without wishing to be bound by theory, the inventors believe the compound (2) may originate from two sources—first, it may be formed during the synthesis of compound (1). Secondly, it is believed that under aqueous acidic conditions an equilibrium occurs between the compounds (1) and (2). This means that the compound (2) can be formed from the compound (1) when the compound (1) is treated with an aqueous acid:

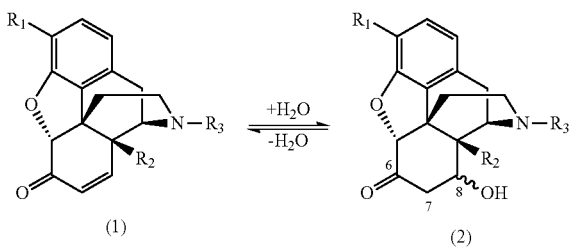

Compound (2) contains a hydroxy substituent at C-8 and, as such, may comprise an 8α-isomer, an 8β-isomer or a combination thereof.

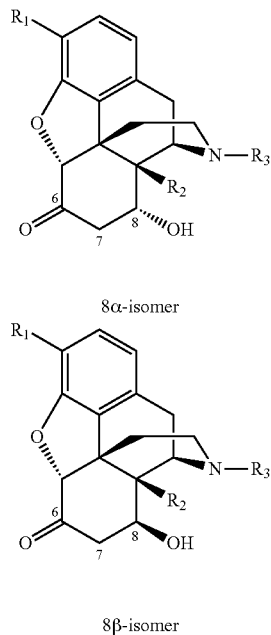

The aqueous acid solution may be prepared from water and an acid selected from the group consisting of acetic acid, phosphoric acid, citric acid, tartaric acid, oxalic acid, hydrochloric acid and hydrobromic acid. In one embodiment, the acid is acetic acid. In another embodiment, the acid is phosphoric acid. In yet another embodiment, the acid is hydrochloric acid.

Any suitable v/v ratio of water:acid may be used. For example, the v/v ratio of water:acid may be from about 100:0.01 to about 0.01:100, such as about 100:1 to about 1:100. In one embodiment, the v/v ratio of water:acid is from about 40:1 to about 60:1.

The quantities of water and/or acid are not particularly limiting provided there is enough water and/or acid to substantially dissolve the compound (1) (and compound (2)) and the water and/or acid do not significantly adversely affect the reaction. The quantity of water present in the catalyst and/or compound (1) (which may also be used wet) may be taken into account when calculating the total quantity of water to be used. The quantity of water present in the acid may also be taken into account when calculating the total quantity of water to be used.

The wt/wt ratio of compound (1): acid may be in the range of about 0.01:200 g/g to about 200:0.1 g/g, such as about 100:1. The ratio of compound (1): water may be in the range of about to about 20:0.005 to about 0.005:20, such as about 0.75:15 to about 15:0.75 g/g, for example about 1:10 to about 1:15 g/g.

The compound (1) (and compound (2)) is substantially dissolved in the water and acid. The dissolution of the compound (1) may be encouraged through the use of an aid such as stirring and/or sonication.

The pH of the initial reaction mixture may be any suitable pH which does not adversely affect the impurity profile of the reaction. In one embodiment, the pH of the initial reaction mixture may be in the range of about ≥1.0 to about <7.0. In some embodiments, the pH may be ≥about 1.5. In some embodiments, the pH may be ≥about 2.0. In some embodiments, the pH may be ≤about 6.5. In some embodiments, the pH may be ≤about 6.0. In some embodiments, the pH may be ≤about 5.5. In one embodiment, the pH of the initial reaction mixture may be in the range of about ≥2.0 to about ≤about 5.0. The pH of the reaction mixture may increase during the course of the reaction and, if desired, the pH may be lowered through the addition of further acid or a solution of acid/water.

The major part of compound (1) is present as a result of charging it as the starting material. A small proportion of compound (1), however, may be generated by dehydrating compound (2) which is present in the starting material as an impurity. Alternatively or in addition, compound (1) may be generated by the hydration of a small proportion of compound (1) to form compound (2) and the subsequent dehydration of compound (2) to reform compound (1). In step (b), the aqueous acidic solution of step (a) is treated such that the compound of formula (2) dehydrates to form a compound of formula (1) and the compound of formula (1) is reduced to form the aqueous acidic solution of the compound of formula (3). It is desirable to minimise the level of the compound (2) in the preparation of the compound (3) because, if it is allowed to remain, a phenomenon known as "ABUK regrowth" may occur. That is, the level of the compound (1) may increase in the compound (3) when the compound (3) is subjected to certain conditions which are commonly used in industry during the preparation of the compounds (3). These conditions include increasing the pH of an acidic solution of a compound (3) in order to precipitate it out of solution and/or drying the so formed free alkaloid. In the present instance, however, the process is carried out under forcing conditions such that the compound (2) dehydrates to the compound (1). The compound (1) is then chemically reduced by hydrogenating the compound (1) in the presence of a hydrogenation catalyst and hydrogen gas to form the compound (3). In the present invention, therefore, the product (i.e. the compound of formula (3)) displays a greater resistance to ABUK regrowth. ABUK regrowth may be assessed by heating samples of the compound (3) at 80° C. overnight in order to force the growth of ABUK. This is known as "stress testing". Stress testing, therefore, is a method for assessing the propensity of a sample of compound (3) to undergo ABUK regrowth.

By "ambient temperature", we mean a temperature of 30° C. or less, such as 0° C. to 30° C., for example 10° C. to 30° C. In the present process, however, the hydrogenation is carried out at one or more temperatures greater than ambient temperature i.e. greater than 30° C. and below the boiling point of the reaction mixture. The boiling point of the reaction mixture may vary depending on the pressure under which the hydrogenation reaction is conducted. In one embodiment, the hydrogenation may be carried out at one or more temperatures in the range of ≥about 75° C. to about ≤about 100° C. In some embodiments, the hydrogenation is carried out at one or more temperatures ≥about 76° C. In some embodiments, the hydrogenation is carried out at one or more temperatures ≥about 77° C. In some embodiments, the hydrogenation is carried out at one or more temperatures ≤about 95° C. In some embodiments, the hydrogenation is carried out at one or more temperatures ≤about 90° C. In some embodiments, the hydrogenation is carried out at one or more temperatures ≤about 85° C. In one preferred embodiment, the hydrogenation is carried out at one or more temperatures in the range of ≥about 77° C. to ≤about 85° C., such as about 80±2° C.

The reaction mixture is generally heated to temperature before the hydrogenation reaction starts. Heating the reaction mixture to temperature may be carried out by purging the reaction vessel with one or more nitrogen/vacuum cycles (e.g. one, two, three or four cycles), optionally followed by one or more hydrogen/vacuum cycles (e.g. one, two or three cycles). The use of hydrogen in the purge cycles may be used on a small scale. However, on a larger, or indeed industrial scale, the hydrogen/vacuum cycles are generally not performed. During purging the reaction mixture may be agitated to encourage removal of dissolved oxygen. After the final purge cycle the vessel may be left under vacuum and agitated (by either stirring or shaking) whilst the vessel is heated. Once the reaction mixture reaches the desired temperature, the hydrogenation reaction may begin by exposing the reaction mixture to hydrogen gas.

The hydrogenation catalyst may be a heterogeneous or homogeneous catalyst, preferably a heterogeneous catalyst. The catalyst (whether heterogeneous or homogeneous) should be selected such that the catalyst preferentially reduces the double bond at C-7 and C-8 rather than reducing the C=O bond at C-6 (see FIG. 1). In one embodiment, the heterogeneous catalyst is a heterogeneous platinum group metal (PGM) catalyst, for example, a heterogeneous palladium or platinum catalyst. In one embodiment, the heterogeneous catalyst is a heterogeneous palladium catalyst. Examples of palladium catalysts include but are not limited to colloidal palladium, palladium sponge, palladium plate or palladium wire. Examples of platinum catalysts include but are not limited to colloidal platinum, platinum sponge, platinum plate or platinum wire.

The heterogeneous PGM catalyst may be a PGM on a solid support. The support may be selected from the group consisting of carbon, alumina, calcium carbonate, barium carbonate, barium sulfate, titania, silica, zirconia, ceria and a combination thereof. When the support is alumina, the alumina may be in the form of alpha-$Al_2O_3$, beta-$Al_2O_3$, gamma-$Al_2O_3$, delta-$Al_2O_3$, theta-$Al_2O_3$ or a combination thereof. When the support is carbon, the carbon may be in the form of activated carbon (e.g. neutral, basic or acidic activated carbon), carbon black or graphite (e.g. natural or synthetic graphite). An example of a heterogeneous PGM catalyst is palladium on carbon. An example of another heterogeneous PGM catalyst is platinum on carbon.

The catalyst loading may be up to about 20 mole %. In one embodiment, the catalyst loading may be up to 10 mole % and, in another embodiment, may be in the range of about 0.001-10 mole %, for example, 0.01-10 mole %. In another embodiment, the catalyst loading may be in the range of about 0.1-10.0 mole %.

While it is typically sufficient for a single charge of hydrogenation catalyst to be added to the reaction mixture, a second or further charge may be added and the hydrogenation continued if it has been determined (e.g. via in-process analysis) that the reaction has not gone to completion and starting material remains.

There is no particular limitation on the pressure at which the hydrogenation is carried out. In this regard, the hydrogenation may conveniently be carried out with an initial hydrogen pressure in the range of up to about 100 psi e.g. about 40±5 psi.

While the use of protecting groups are generally not required in the present process, if it is found that the compound (1) has one or more substituents which may be adversely affected during the reduction, such as 3-hydroxy or 17-NH groups, these may be protected in a conventional manner. Alternatively, if these substituents have been protected prior to the present process (for example, in steps leading to the synthesis of the compound (1)), the protecting group(s) may be selected such that simultaneous hydrogenation of the compound (1) and deprotection occurs to form the compound (3). Suitable protecting groups which are capable of withstanding hydrogenation or are removed during hydrogenation are known in the art (see, for example, "Protective Groups in Organic Chemistry", Peter G. M. Wuts and Theodora W. Greene, Wiley Blackwell) and include unsubstituted or substituted benzyl groups.

The hydrogenation reaction is carried out for a period of time until it is determined that the reaction is complete. Completion of the reaction may be determined by in-process analysis or by identifying that there is no longer an uptake of hydrogen gas. Typically the hydrogenation is complete within about 4 hours or less. The period of time over which the hydrogenation is carried out should be taken in account when carrying out the present process as it may adversely affect the impurity profile of the resulting compound (3). For example, when the compound (1) is nor-14-hydroxymorphinone and the compound (3) is noroxymorphone, it is generally not desirable to extend the duration of the hydrogenation as it has been found that this may lead to increased levels of 6β-noroxymorphol. 6β-Noroxymorphol is a known impurity in the synthesis of noroxymorphone and which may be identified using the HPLC method provided below. Without wishing to be bound by theory, it is believed that 3-noroxymorphol may be produced from noroxymorphone via the ketone reduction at C-6 (see FIG. 1). Extended hydrogenation therefore may lower the yield of the desired product through its further reaction, as well as generating an increased level of an unwanted impurity.

On completion of the reaction, the reaction vessel may be cooled and purged to remove excess hydrogen gas (or vice versa). The hydrogenation catalyst may be removed by any appropriate method, such as filtration, and the filtrate (containing the compound (3)) may be further treated as desired.

In one embodiment, the present process provides an aqueous acidic solution of compound (3) comprising ≤about 0.05 area % of the compound of formula (1) as determined by HPLC, such ≤about 0.04 area %, for example, ≤about 0.03 area %. In some embodiments, the process provides an aqueous acidic solution of compound (3) comprising ≤about 0.02 area % of the compound of formula (1), for example, ≤about 0.01 area %. It is envisaged that, in some embodiments, the process could provide an aqueous acidic solution of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide an aqueous acidic solution of compound (3) comprising compound of formula (1) in a non-detectable amount (as determined by HPLC).

In another embodiment, the process further comprises treating the aqueous acidic solution of compound (3) to form solid salts of compound (3) (i.e. acid adducts of the compound (3) which are in a solid form, such as a precipitate). Examples of solid salts include but are not limited to noroxymorphone acetate or noroxymorphone hydrochloride. It is also envisaged that the aqueous acidic solution compound (3) may undergo a salt exchange to form an aqueous acidic solution of compound (3) comprising a different acid. For example, a solution of noroxymorphone acetate may undergo a salt exchange to form a solution of noroxymorphone hydrochloride.

In one embodiment, the solid salt of compound (3) comprises ≤about 0.05 area % of the compound of formula (1) as determined by HPLC, such ≤about 0.04 area %, for example, ≤about 0.03 area %. In some embodiments, the solid salt of compound (3) comprises ≤about 0.02 area % of the compound of formula (1), for example, ≤about 0.01 area %. It is envisaged that, in some embodiments, the process could provide a solid salt of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide an aqueous acidic solution of compound (3) comprising compound of formula (1) in a non-detectable amount (as determined by HPLC).

In yet another embodiment, the process further comprises treating the aqueous acidic solution of compound (3) at about 45-50° C. with a base to form the alkaloid of compound (3). An example of a suitable base is ammonium hydroxide. Sufficient base is typically added so that the compound (3) precipitates out of solution. Generally, precipitates of compound (3) start to become visible at about pH 7 and typically sufficient base is added to increase the pH to about 8.5-9.0 or above. This ensures that the compound (3) is in free base form, as well as allowing maximum recovery of the compound (3). The alkaloid of compound (3) may be collected (e.g. by filtration), optionally washed one or more times (e.g. with Alcohol M, which is 96% ethanol denatured with 4% methanol) and dried.

In another embodiment, the process further comprises treating the solid salt of compound (3) to form the free alkaloid. This may be carried out by redissolving the solid salt to form a solution of the salt of compound (3) and treating the solution with a base as described above. The alkaloid of the compound (3) may be collected (e.g. by filtration), optionally washed one or more times and dried.

Howsoever the alkaloid of compound (3) is prepared, the alkaloid may comprise ≤about 0.05 area % of the compound of formula (1) as determined by HPLC, such ≤about 0.04 area %, for example, ≤about 0.03 area %. In some embodiments, the alkaloid of compound (3) comprises ≤about 0.02 area % of the compound of formula (1), for example, ≤about 0.01 area %. It is envisaged that, in some embodiments, the process could provide the alkaloid of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide the alkaloid of compound (3) comprising compound of formula (1) in a non-detectable amount (as determined by HPLC).

In a second aspect, the invention provides a process for preparing a compound of formula (3), the process comprising the steps of:

(I) hydrogenating an aqueous acidic solution comprising a compound of formula (1) and, as an impurity, a compound of formula (2), wherein the hydrogenation is carried out at ambient temperature in the presence of a hydrogenation catalyst and hydrogen gas; and (II) hydrogenating the product of step (I) at one or more temperatures greater than ambient temperature in the presence of a hydrogenation catalyst and hydrogen gas to form an aqueous acidic solution of the compound of formula (3) comprising ≤0.05 area % of the compound of formula (1) as determined by HPLC and ≤2.00 area % of a compound of formula (4) as determined by HPLC,

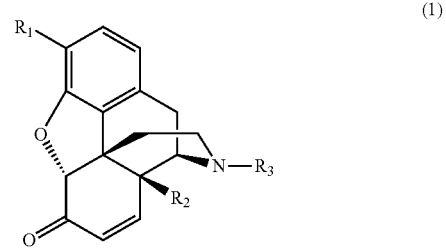

(1)

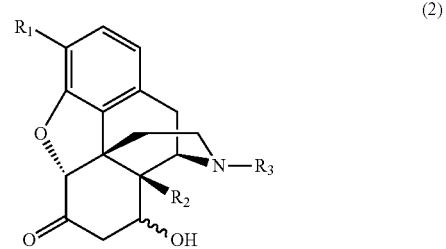

(2)

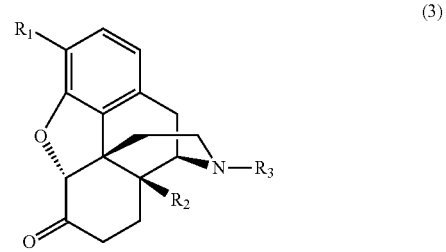

(3)

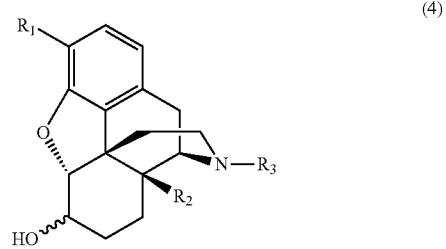

(4)

wherein for the compounds of formulae (1), (2), (3) and 4:
i) $R_1$ is —OH, $R_2$ is —OH and $R_3$—H; or
ii) $R_1$ is —OCH$_3$, $R_2$ is —H and $R_3$—CH$_3$; or iii) $R_1$ is —OH, $R_2$ is —H and $R_3$—$CH_3$; or
iv) $R_1$ is —$OCH_3$, $R_2$ is —H and $R_3$—H; or
v) $R_1$ is —OH, $R_2$ is —H and $R_3$—H; or
vi) $R_1$ is —$OCH_3$, $R_2$ is —OH and $R_3$—H.

Compounds (1), (2), (3) and the acidic solution are as generally described above. In one preferred embodiment, $R_1$ is —OH, $R_2$ is —OH and $R_3$—H for the compounds (1), (2), (3) and (4).

The compound of formula (4) is produced as an impurity in the transformation of compound (1) to compound (3). The compound (4) contains a hydroxy substituent at C-6 and, as such, may comprise a 6α-isomer, a 6β-isomer or a combination thereof.

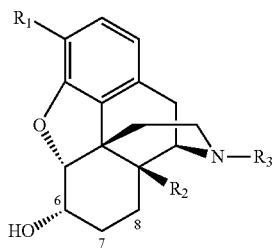

6α-isomer

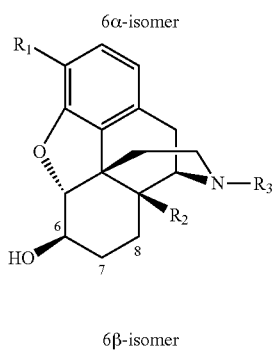

6β-isomer

Carrying out a hydrogenation reaction at temperatures greater than ambient on some compounds of formula (1) may result in increased levels of the compound of formula (4) being produced. For example, during the synthesis of noroxymorphone, increased levels of 6α-noroxymorphol may occur during the hydrogenation of nor-14-hydroxymorphinone at one or more temperatures above ambient.

As can be seen from FIG. 1, without wishing to be bound by theory, it is believed that 6α-noroxymorphol is generated from 14-hydroxynormorphinone and that 6β-noroxymorphol from noroxymorphone. Accordingly, it is desirable to develop a process which is capable of minimising or eliminating the production of the compound (4). Without wishing to be bound by theory, therefore, it is believed that the two-step process is suitable for (a) minimising or eliminating the production of compound (4) from compound (1), (b) dehydrating compound (2) to compound (1) under forcing conditions, and (c) chemically reducing compound (1) to form compound (3). As described above, the product of the reaction (i.e. the compound of formula (3)) displays a greater resistance to ABUK regrowth.

In step (I), therefore, the aqueous acidic solution comprising the compound of formula (1) and, as an impurity, the compound of formula (2) is hydrogenated at ambient temperature in the presence of a hydrogenation catalyst and hydrogen gas.

By "ambient temperature", we mean a temperature of 30° C. or less such as 0° C. to 30° C., for example 10° C. to 30° C. The hydrogenation conditions described above for the first aspect (other than the temperature) generally apply to this aspect of the invention.

In step (II), the product of step (I) is hydrogenated at one or more temperatures greater than ambient temperature in the presence of a hydrogenation catalyst and hydrogen gas to form an aqueous acidic solution of the compound of formula (3) comprising ≤0.05 area % of the compound of formula (1) as determined by HPLC and ≤2.00 area % of a compound of formula (4) as determined by HPLC. The hydrogenation conditions described above for the first aspect (including the temperature) generally apply to this aspect of the invention.

In one embodiment, the hydrogen gas present in step (I) may be substantially removed from the reaction vessel before the reaction mixture is heated to one or more temperatures above ambient. The hydrogen gas may be removed from the reaction vessel by purging. Once the reaction mixture is at the desired temperature, the reaction mixture may be exposed once again to hydrogen.

On completion of the reaction, the reaction vessel may be cooled and purged to remove excess hydrogen gas (or vice versa). The hydrogenation catalyst may be removed by any appropriate method, such as filtration, and the filtrate (containing the compound (3)) may be further treated as desired.

The process forms an aqueous acidic solution of the compound of formula (3) comprising ≤0.05 area % of the compound of formula (1) as determined by HPLC and ≤2.00 area % of a compound of formula (4) as determined by HPLC.

In one embodiment, the process provides an aqueous acidic solution of compound (3) comprising ≤about 0.04 area % of compound (1) as determined by HPLC, for example, ≤about 0.03 area %. In some embodiments, the process provides an aqueous acidic solution of compound (3) comprising ≤about 0.02 area % of the compound of formula (1), for example, ≤about 0.01 area %. It is envisaged that, in some embodiments, the process could provide an aqueous acidic solution of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide an aqueous acidic solution of compound (3) comprising compound of formula (1) in a non-detectable amount (as determined by HPLC).

In one embodiment, the process provides an aqueous acidic solution of comprising ≤1.75 area % of a compound of formula (4) as determined by HPLC, such as ≤1.50 area %, for example, ≤1.25 area % or ≤1.00 area %.

In another embodiment, the process further comprises treating the aqueous acidic solution of compound (3) to form solid salts of compound (3) (i.e. acid adducts of the compound (3) which are in a solid form, such as a precipitate). Examples of solid salts include but are not limited to noroxymorphone acetate or noroxymorphone hydrochloride. It is also envisaged that the aqueous acidic solution compound (3) may undergo a salt exchange to form an aqueous acidic solution of compound (3) comprising a different acid. For example, a solution of noroxymorphone acetate may undergo a salt exchange to form a solution of noroxymorphone hydrochloride.

In one embodiment, the solid salt of compound (3) comprises ≤about 0.05 area % of the compound of formula (1) as determined by HPLC, such ≤about 0.04 area %, for example, ≤about 0.03 area %. In some embodiments, the solid salt of compound (3) comprises ≤about 0.02 area % of the compound of formula (1), for example, ≤about 0.01 area %. It is envisaged that, in some embodiments, the process could provide a solid salt of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide a solid salt of compound (3) comprising compound of formula (1) in a non-detectable amount (as determined by HPLC).

In another embodiment, the solid salt of compound (3) comprises ≤1.75 area % of a compound of formula (4) as determined by HPLC, such as ≤1.50 area %, for example, ≤1.25 area % or ≤1.00 area %. In some embodiments, the solid salt of compound (3) comprises ≤1.00 area % of the 6α-isomer of a compound of formula (4), such as ≤0.75 area %, for example, ≤0.50 area % or ≤0.40 area %. In some embodiments, the solid salt of compound (3) comprises ≤1.00 area % of the 6β-isomer of a compound of formula (4), such as ≤0.75 area %, for example, ≤0.50 area % or ≤0.40 area %.

In yet another embodiment, the process further comprises treating the aqueous acidic solution of compound (3) at about 45-50° C. with a base to form the alkaloid of compound (3). An example of a suitable base is ammonium hydroxide. Sufficient base is typically added so that the compound (3) precipitates out of solution. Generally, precipitates of compound (3) start to become visible at about pH 7 and typically sufficient base is added to increase the pH to about 9. This ensures that the compound (3) is in free base form, as well as allowing maximum recovery of the compound (3). The alkaloid of compound (3) may be collected (e.g. by filtration), optionally washed one or more times (e.g. with Alcohol M) and dried.

In another embodiment, the process further comprises treating the solid salt of compound (3) to form the free alkaloid. This may be carried out by redissolving the solid salt to form a solution of the salt of compound (3) and treating the solution with a base as described above. The compound (3) alkaloid may be collected (e.g. by filtration), optionally washed one or more times and dried.

Howsoever the alkaloid of compound (3) is prepared, the alkaloid may comprise ≤about 0.05 area % of the compound of formula (1) as determined by HPLC, such as ≤about 0.04 area %, for example, ≤about 0.03 area %. In some embodiments, the alkaloid of compound (3) comprises ≤about 0.02 area % of the compound of formula (1), for example, ≤about 0.01 area %. It is envisaged that, in some embodiments, the process could provide the alkaloid of compound (3) comprising ≤about 0.005 area % of the compound of formula (1), such as ≤about 0.004 area %, for example ≤about 0.003 area % e.g. ≤about 0.002 area % or ≤about 0.001 area %. In some embodiments, the process may provide the alkaloid of compound (3) comprising compound of formula (1) in a non-detectable amount (as determined by HPLC).

In another embodiment, the alkaloid of compound (3) comprises ≤1.75 area % of a compound of formula (4) as determined by HPLC, such as ≤1.50 area %, for example, ≤1.25 area % or ≤1.00 area %. In some embodiments, the solid salt of compound (3) comprises ≤1.00 area % of the 6α-isomer of a compound of formula (4), such as ≤0.75 area %, for example, ≤0.50 area % or ≤0.40 area %. In some embodiments, the solid salt of compound (3) comprises ≤1.00 area % of the 6β-isomer of a compound of formula (4), such as ≤0.75 area %, for example, ≤0.50 area % or ≤0.40 area %.

In another aspect, the present invention provides a compound of formula (3) comprising a compound of formula (1) in an amount ≤0.01 area % as determined by HPLC,

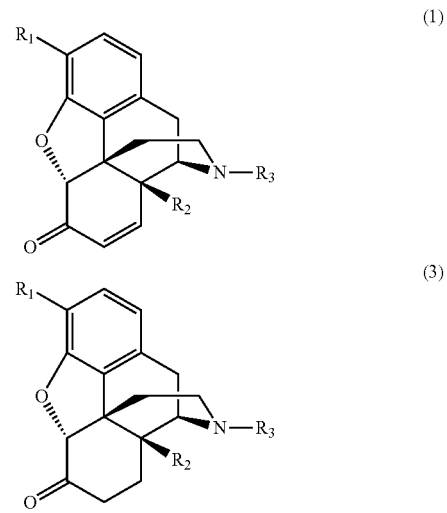

wherein for the compounds of formulae (1) and (3):
i) $R_1$ is —OH, $R_2$ is —OH and $R_3$—H; or
ii) $R_1$ is —OCH$_3$, $R_2$ is —H and $R_3$—CH$_3$; or
iii) $R_1$ is —OH, $R_2$ is —H and $R_3$—CH$_3$; or
iv) $R_1$ is —OCH$_3$, $R_2$ is —H and $R_3$—H; or
v) $R_1$ is —OH, $R_2$ is —H and $R_3$—H; or
vi) $R_1$ is —OCH$_3$, $R_2$ is —OH and $R_3$—H.

In one preferred embodiment, $R_1$ is —OH, $R_2$ is —OH and $R_3$—H for the compounds (1) and (3).

In one embodiment, the compound of formula (3) and compound of formula (1) (if present) are solid salts (i.e. are acid adducts and are in a solid form, such as a precipitate). The solid salts may be selected from the group consisting of the acetate, phosphate, tartrate, citrate, hydrochloride or hydrobromide. In one embodiment, the solid salt may be an acetate salt. In another embodiment, the solid salt may be a phosphate salt. In yet another embodiment, the solid salt may be a tartrate salt. In another embodiment, the solid salt may be a hydrochloride salt.

In one embodiment, the compound of formula (3) and compound of formula (1) (if present) are solid alkaloids (i.e. are free bases and are in solid form, such as a precipitate).

The compound of formula (1) is present in an amount ≤0.01 area % as determined by HPLC. It is envisaged that, in some embodiments, the compound (1) may be present in an amount ≤about 0.005 area %, such as ≤about 0.004 area %, for example ≤about 0.003 area % e.g. ≤about 0.002 area % or ≤about 0.001 area %. In some embodiments, the compound (1) may be present in a non-detectable amount (as determined by HPLC).

Compound (3) or salt thereof (prepared according the aspects described above) may be suitable as intermediates for the preparation of other morphinan-6-one compounds. For example, noroxymorphone is a key intermediate in the synthesis of naltrexone, naloxone, nalmefene and 6-keto-nalbuphine:

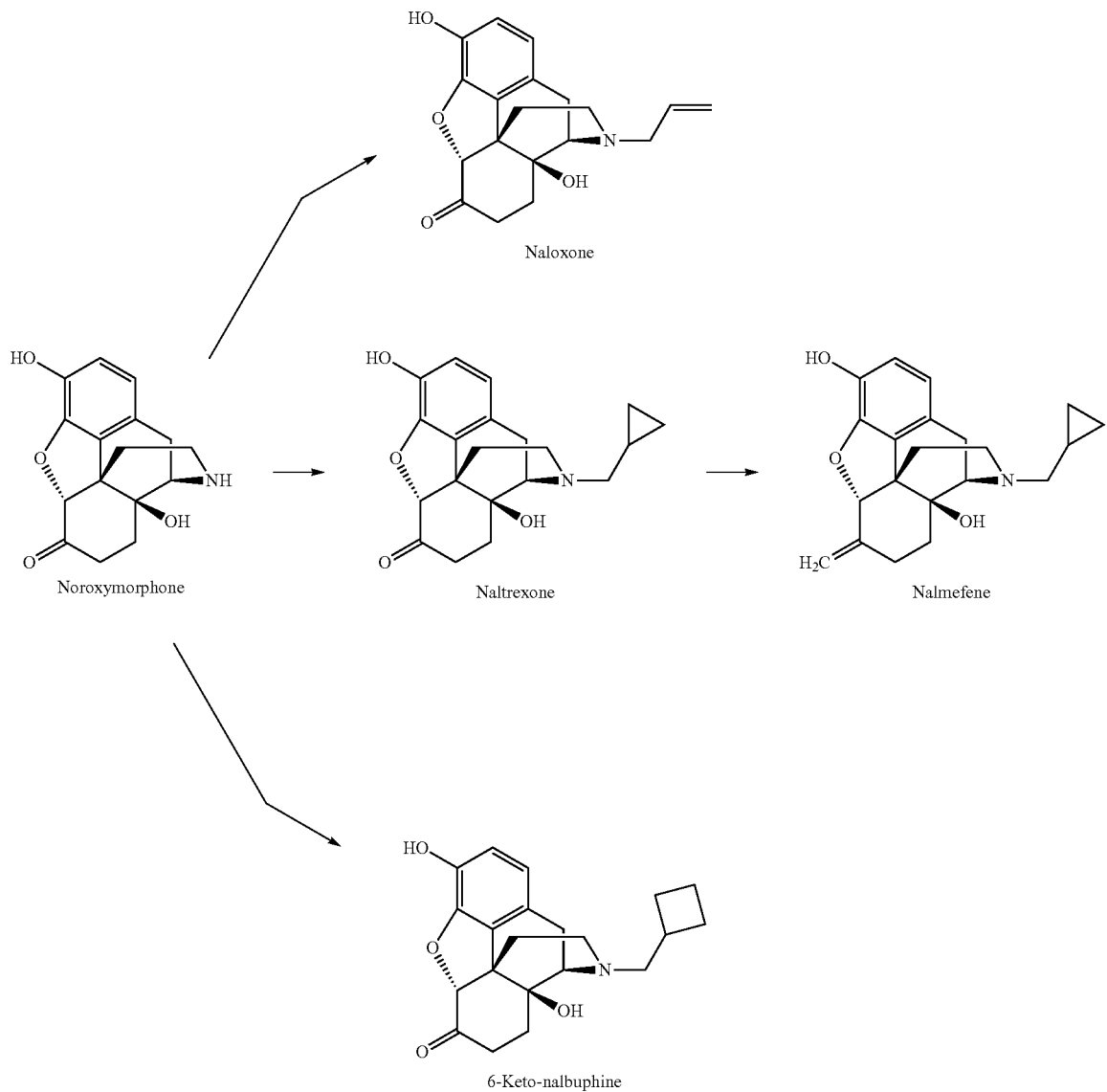

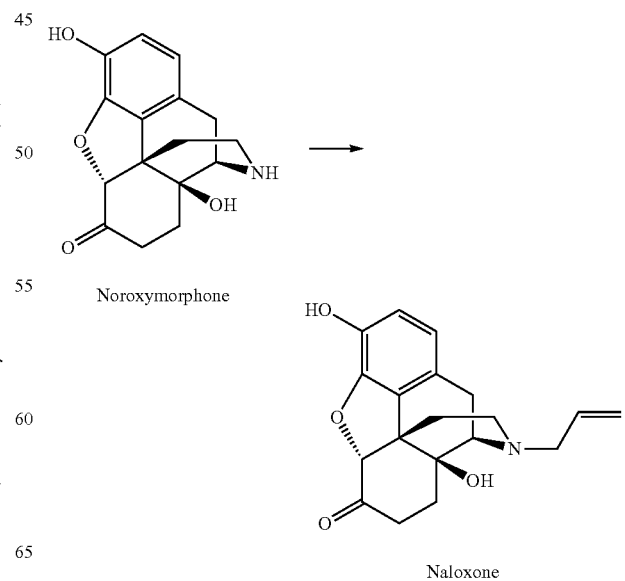

Naloxone, naltrexone, nalmefene, and 6-keto-nalbuphine may be prepared by known methods. In this regard, naloxone may be prepared by reacting noroxymorphone with sodium hydrogencarbonate and allyl bromide (see for example U.S. Pat. No. 3,254,088 to Lewenstein et al). Naltrexone and 6-keto-nalbuphine may be prepared according to the reductive alkylation method described in U.S. Pat. No. 8,318,937 and U.S. Pat. No. 8,119,803 (to Johnson Matthey PLC). Nalmefene may be prepared from naltrexone using methylenetriphenylphosphorane (Hahn et al, J. Med. Chem., 18, 259 (1975)).

Noroxymorphone prepared according to the processes of the present invention comprises a low level of ABUK and, furthermore, displays a greater resistance to ABUK regrowth. As such, products prepared from noroxymorphone may also exhibit lower levels of ABUK and a greater resistance to ABUK regrowth. For example, noroxymorphone prepared according to the processes of the present invention has been allylated to prepare naloxone comprising ≤35 ppm of the ABUK 7,8-didehydronaloxone.

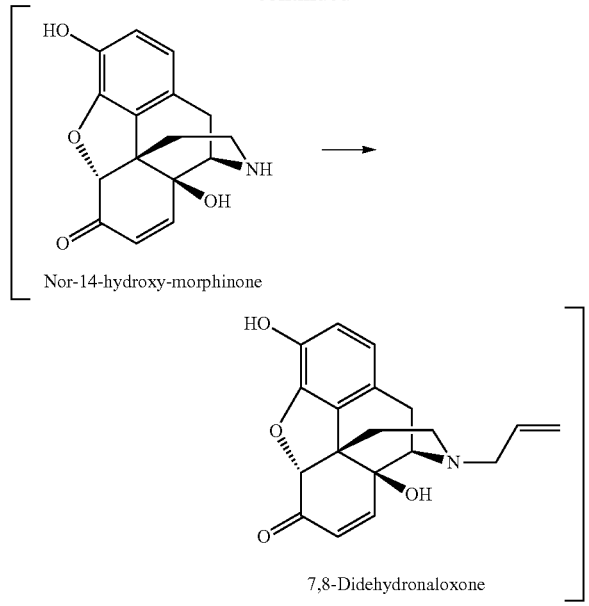

Embodiments and/or optional features of the invention have been described above. Any aspect of the invention may be combined with any other aspect of the invention, unless the context demands otherwise. Any of the embodiments or optional features of any aspect may be combined, singly or in combination, with any aspect of the invention, unless the context demands otherwise.

The invention will now be described by way of the following non-limiting Examples and with reference to the accompanying figures in which:

FIG. 1 illustrates the conversion of nor-14-hydroxymorphinone (a compound of formula (1)) to noroxymorphone (a compound of formula (3)). The figure also illustrates 8,14-dihydroxy-7,8-dihydromorphinone (a compound of formula (2)) and the equilibrium between it and nor-14-hydroxymorphinone. The formation of α-noroxymorphol and 3-noroxymorphol is also shown.

Figure 2:
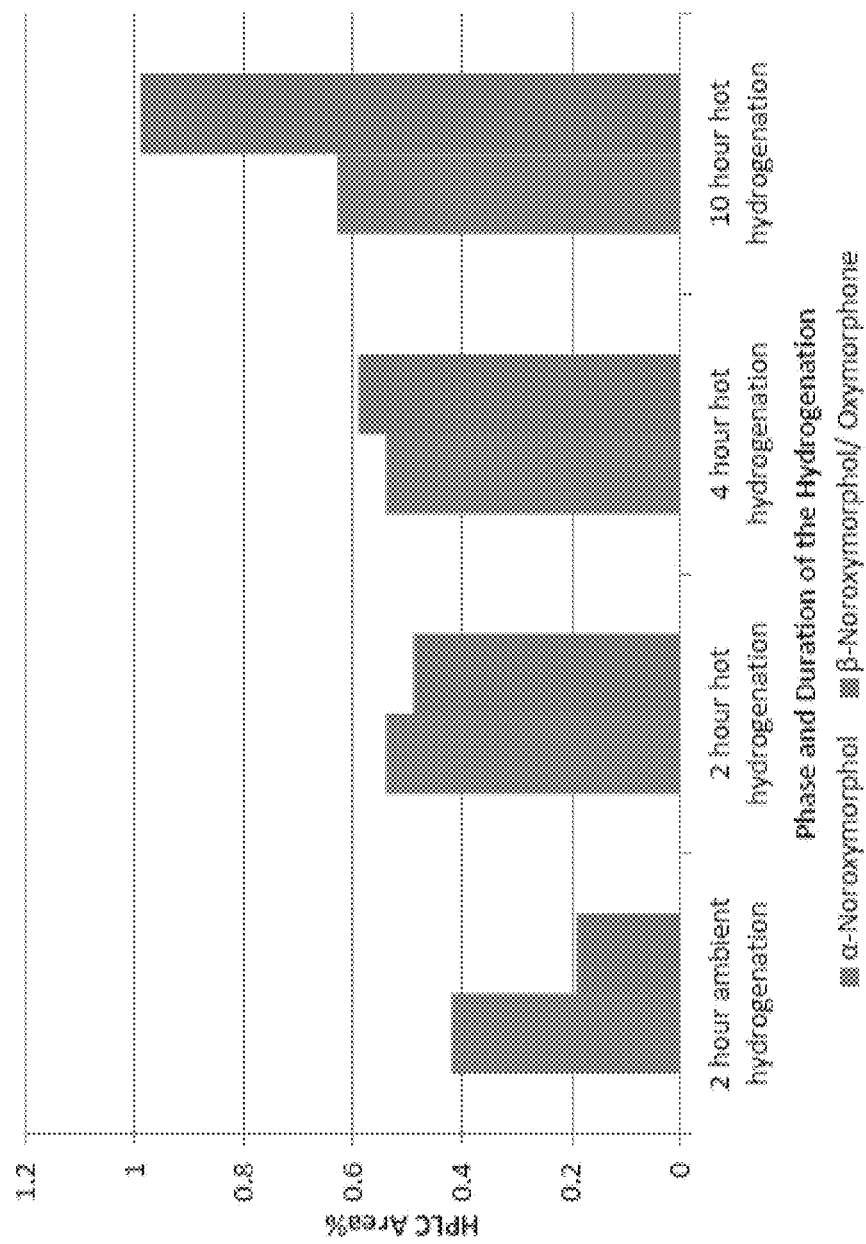

FIG. 2 is a graph comparing related substances levels (6α-noroxymorphol, and 6β-noroxymorphol/oxymorphone) in hydrogenation liquors where the duration of the 80° C. hydrogenation was varied.

EXAMPLES

HPLC Method

Naloxone Hydrochloride European Pharmacopeia Method

| Column | Zorbax Eclipse XDB-C8 5 microns 12.5 cm × 4.0 mm |
|---|---|
| Mobile Phase | Prepare a solution as follows: dissolve 1.17 g sodium octanesulphonate in 1000 ml water, adjust to pH 2.0 with a 50% v/v solution of phosphoric acid |
| | A 20 ml acetonitrile, 40 ml THF and 940 ml of above solution |
| | B 170 ml acetonitrile, 40 ml THF and 790 ml of above solution |
| Flow rate | 1.5 ml/minute |
| Temperature | 40° C. |
| Detector | UV @ 230 nm |
| Injection Volume | 20 microlitres |
| Run Time | 45 minutes |

Linear Gradient:

| Time (min) | A % v/v | B % v/v |
|---|---|---|
| 0 | 100 | 0 |
| 40 | 0 | 100 |
| 50 | 0 | 100 |
| 55 | 100 | 0 |
| 65 | 100 | 0 |

Sample Preparation

Noroxymorphone Liquors

The hydrogenation liquors were sampled (100 mL) and diluted in a 5 mL volumetric flask with 0.1M HCl to the mark.

Noroxymorphone Solids

Sample 25 mg of solid and dilute to the mark in 25 mL volumetric flask with 0.1 M HCl.

Naloxone in Process Check (IPC) Liquors

Sample 300 μL of reaction liquors and dilute to the mark in a 5 mL volumetric flask with 0.1 M HCl.

Naloxone Solids

Sample ~40 mg of solids and dilute to the mark in a 25 mL volumetric flask with 0.1 M HCl.

Retention Times of Known Impurities in Noroxymorphone

| Approximate Retention Time (min) | Relative Retention Time | Substance |
|---|---|---|
| 10.5 | 0.70 | 6α-Noroxymorphol |
| 12 | 0.81 | 6β-Noroxymorphol/Oxymorphone |
| 16 | 1.10 | Nor-14-hydroxymorphinone |

Retention Times of Known Impurities in Naloxone

| Approximate Retention Time (min) | Relative Retention Time | Substance |
|---|---|---|
| 11.5 | 0.83 | Noroxymorphone |
| 43 | 3.1 | 3-O-Allylnaloxone |
| 46.5 | 3.4 | 2,2-Bisnaloxone |

Experimental Methods

The following are the general experimental procedures. Experimental variables e.g. pressure were altered depending on the parameter investigated. The masses and volumes used for each material input for each experiment given in the text are supplied in the tables below along with any deviations from the general experimental method.

Apparatus Used

The hydrogenations were carried out on either a Parr Shaker or Stirrer hydrogenator. All basifications were carried out in appropriately sized flange flasks fitted with a thermocouple, condenser and a temperature controlled isomantle.

Analysis

The analysis was carried out using High Performance Liquid Chromatography (HPLC) using the Naloxone European Pharmacopeia method. The method was used as good separation of the majority of impurities with Noroxymorphone is achieved.

A) General Experimental Outline for Single Hydrogenation Followed by Basification
  General Ambient Only Hydrogenation
1) Charge Nor-14-hydroxymorphinone (A g) to a hydrogenation flask. Add water (B mL), 85% w/w phosphoric acid (C mL) and 5% Pd/C catalyst (D g).
2) Fit the vessel to the hydrogenator and purge the vessel with nitrogen (3×) and hydrogen (3×).
3) Pressurise the hydrogenation vessel with hydrogen to 40±3 PSI.
4) Commence the agitation (the shaker hydrogenator is fixed rate, for the stirrer hydrogenator fitted with a gas entrainment stirrer the agitator was set to 1200 rpm).
5) Allow the hydrogenation reaction to continue for 2 hours.
6) Turn off the agitation, vent the hydrogen and remove the hydrogenation vessel from the hydrogenator.
7) Deposit harbolite (~2 g) on a 42 mm filter.
8) Filter the hydrogenation liquors through the harbolite and was the filter with water (A mL).
  Isolation of Noroxymorphone Alkaloid
9) Charge the hydrogenation liquors to an appropriately sized flange flask, fitted with a thermocouple, temperature controlled isomantle, stirrer and condenser.
10) Heat the batch to 45-50° C.
11) Mix Ammonia S.G. 0.88 (E mL) with water (E mL) to make 50:50 aqueous ammonia.
12) pH adjust the batch with the aqueous ammonia to pH 8.5-9.0, checking the pH with a calibrated pH meter.
13) Stir the batch at 45-50° C. for 15 minutes and recheck the pH is within range.
14) Allow the batch to cool to ambient temperature and stir for 2 hours.
15) Filter the batch under suction filtration and was the filter cake with water (A mL) and Alcohol M (A mL). Alcohol M is 96% ethanol denatured with 4% methanol.
16) Dry the Noroxymorphone Alkaloid in a 55° C. oven overnight.

B) General Experimental Outline for Noroxymorphone Pure Process (Low ABUK Hydrogenation and Basification
  Low ABUK Hydrogenation of Nor-14-Hydroxymorphinone to Noroxymorphone
1) Charge Nor-14-hydroxymorphinone (A g) to a hydrogenation flask. Add water (B mL), 85% w/w phosphoric acid (C mL) and 5% Pd/C catalyst (D g).
2) Fit the vessel with the heating jacket on to the hydrogenator and purge the vessel with nitrogen (3×) and hydrogen (3×).
3) Pressurise the hydrogenation vessel with hydrogen to 40±3 PSI.
4) Commence the agitation (the shaker hydrogenator is fixed rate, for the stirrer hydrogenator fitted with a gas entrainment stirrer the agitator was set to 1200 rpm).
5) Allow the ambient hydrogenation reaction to continue for 2 hours.
6) Evacuate the flask and turn the heater on to the set point 80° C.
7) Allow the flask to heat to 80±2° C. with agitation.
8) Once a temperature of 80±2° C. is attained, pressurise the hydrogenation vessel with hydrogen to 40±3 PSI.
9) Allow the hydrogenation reaction to continue for 2 hours.
10) Evacuate the hydrogenation vessel and allow the reaction liquors to cool to ~30° C.
11) Turn off the agitation and remove the hydrogenation vessel from the hydrogenator.
12) Deposit harbolite (~2 g) on a 42 mm filter.
13) Filter the hydrogenation liquors through the harbolite and wash the filter with water (A mL).
  Isolation of Noroxymorphone Alkaloid
14) Charge the hydrogenation liquors to an appropriately sized flange flask, fitted with a thermocouple, temperature controlled isomantle, stirrer and condenser.
15) Heat the batch to 45-50° C.
16) Mix Ammonia S.G. 0.88 (E mL) with water (E mL) to make 50:50 aqueous ammonia.
17) pH adjust the batch with the aqueous ammonia to pH 8.5-9.0, checking the pH with a calibrated pH meter.
18) Stir the batch at 45-50° C. for 15 minutes and recheck the pH is within range.
19) Allow the batch to cool to ambient temperature and stir for 2 hours.
20) Filter the batch under suction filtration and wash the filter cake with water (A mL) and Alcohol M (A mL). Alcohol M is 96% ethanol denatured with 4% methanol.
21) Dry the Noroxymorphone Alkaloid in a 55° C. oven overnight.

Example 1

The following experiments were carried out using a Parr Shaker hydrogenator.

| Expt. | A | B | C | D | E | Comments |
|---|---|---|---|---|---|---|
| 1.1* | 3.75 | 51 | 1 | 0.037 | — | Method A, steps 1-8 carried out. |
| 1.2‡ | 3.75 | 51 | 1 | 0.037 | — | Method A was carried out where steps 3-6 (of Method A) were replaced by steps 7-10 of Method B. |
| 1.3‡ | 3.75 | 49 | 3 | 0.037 | — | Method A was carried out where steps 3-6 (of Method A) were replaced by steps 7-10 of Method B. C = acetic acid. |

*Comparative
‡According to the invention

HPLC Analysis:

| Expt. | Reaction temp. (° C.) | 6α-Noroxymorphol (area %) | 6β-Noroxymorphol/ Oxymorphone (area %) |
|---|---|---|---|
| 1.1* | Ambient | 0.41 | 0.43 |
| 1.2‡ | 80 | 1.39 | 0.10 |
| 1.3‡ | 80 | 1.22 | 0.14 |

*Comparative
‡According to the invention

Example 2

Example 2 was carried out where the duration of the ambient phase of the hydrogenation was kept at 2 hours and the length of the 80° C. hydrogenation of Method B was varied at 2, 4 and 10 hours. The hydrogenation liquors were analysed for related substances using the European Pharmacopeia HPLC Method provided above.

The experiment was carried out using a Parr Shaker hydrogenator.

| A | B | C | D | E | Comments |
|---|---|---|---|---|---|
| 20 | 275 | 5 | 0.2 | 5 | Method B, steps 1-21 carried out. Liquors split into three lots after the ambient hydrogenation; Examples 2.2, 2.3 and 2.4 were hydrogenated hot (steps 7-10) for 2, 4 and 10 hours respectively. |

HPLC Analysis:

| Sample | Example 2.1 | Example 2.2 | Example 2.3 | Example 2.4 |
| --- | --- | --- | --- | --- |
| Related Substances (Area %) | 2 hr ambient hydrogenation | 2 hr 80° C. hydrogenation | 4 hr 80° C. hydrogenation | 10 hour 80° C. hydrogenation |
| 6α-Noroxymorphol | 0.42 | 0.54 | 0.54 | 0.63 |
| 6β-Noroxymorphol/Oxymorphone | 0.19 | 0.49 | 0.59 | 0.99 |
| Nor-14-hydroxymorphinone | 0.02 | — | — | — |

| Sample | Example 2.5 | Example 2.6 | Example 2.7 |
| --- | --- | --- | --- |
| Related Substances (Area %) | (Liquors put through to 80° C. hydrogenation) | Noroxymorphone from Example 2.2 | Noroxymorphone from Example 2.3 | Noroxymorphone from Example 2.4 |
| 6α-Noroxymorphol | n/a | 0.39 | 0.48 | 0.42 |
| 6β-Noroxymorphol/Oxymorphone | n/a | 0.50 | 0.58 | 0.68 |
| Nor-14-hydroxymorphinone | n/a | 0.01 | 0.01 | — |

The data above demonstrates that the levels of nor-14-hydroxymorphinone are 0.01 area % or less for the high temperature hydrogenations (see Examples 2.2-2.7). In Examples 2.2-2.4 and 2.7, the ABUK (nor-14-hydroxymorphinone) was non-detectable by HPLC.

FIG. 2 illustrates the results provided in the table above where it can be seen that the level of α-noroxymorphol does not substantially increase greatly after the 2 hours 80° C.

Example 3 (Comparative)

The following experiment was carried out using a Parr stirrer hydrogenator.

| A | B | C | D | E | Comments |
| --- | --- | --- | --- | --- | --- |
| 20 | 275 | 5 | 0.2 | 16 | Method A used (steps 1-16) |

HPLC Analysis:

| Sample | Example 3.1 | Example 3.2 | Example 3.3 |
| --- | --- | --- | --- |
| | Hydrogenation liquors after hydrogenation for 2 hrs at ambient temperature | Isolated noroxymorphone (i.e. product obtained after Method A, step 16) | Noroxymorphone dried at 80° C. |
| Nor-14-hydroxy-morphinone (ppm, corrected for LOD) | 41.8 | 280.04 | 301.52 |

The ABUK level in the hydrogenation liquors appeared low at 41.8 ppm. However, regrowth of the ABUK occurred upon basification of the liquors at 45° C. with the ABUK level increasing to 280 ppm. Furthermore, on stress-testing the isolated noroxymorphone at 80° C., the ABUK level increased even more to 301.52 ppm.

This Example can be compared with Example 2 where the ABUK level consistently remained at 0.01 area % (i.e. 100 ppm) or less throughout the experiment. In Examples 2.2-2.4 and 2.7, the ABUK was non-detectable by HPLC.

The invention claimed is:

1. A process for preparing a compound of formula (3), comprising:

treating an aqueous acidic solution comprising a compound of formula (1) and a compound of formula (2), wherein the compound of formula (2) dehydrates to form a compound of formula (1) and the compound of formula (1) is reduced to form the compound of formula (3),

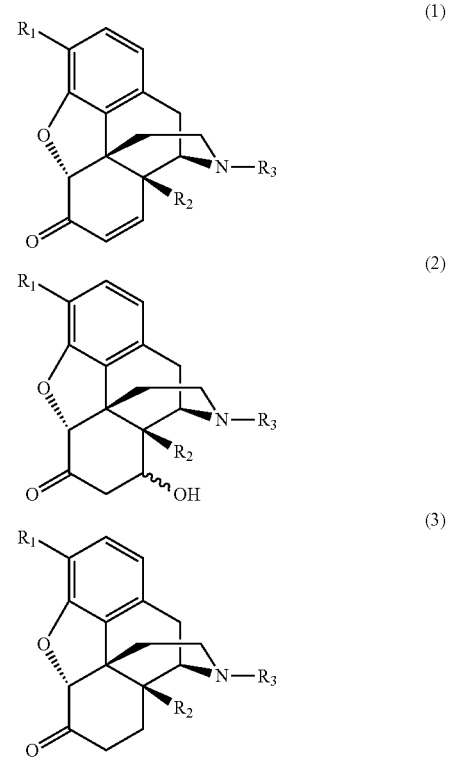

wherein:

the process is carried out at one or more temperatures greater than ambient in the presence of a hydrogenation catalyst and hydrogen gas; and the aqueous acidic solution is heated to a temperature above ambient before it is exposed to the hydrogen gas; and wherein for the compounds of formulae (1), (2) and (3):
i) $R_1$ is —OH, $R_2$ is —OH and $R_3$—H; or
ii) $R_1$ is —OCH$_3$, $R_2$ is —H and $R_3$—CH$_3$; or
iii) $R_1$ is —OH, $R_2$ is —H and $R_3$—CH$_3$; or
iv) $R_1$ is —OCH$_3$, $R_2$ is —H and $R_3$—H; or
v) $R_1$ is —OH, $R_2$ is —H and $R_3$—H; or
vi) $R_1$ is —OCH$_3$, $R_2$ is —OH and $R_3$—H.

2. The process according to claim 1, wherein $R_1$ is —OH, $R_2$ is —OH and $R_3$—H.

3. The process according to claim 1, wherein the acid in the aqueous acidic solution is acetic acid, phosphoric acid, citric acid, tartaric acid, oxalic acid, hydrochloric acid, hydrobromic acid, or a mixture thereof.

4. The process according to claim 1, wherein the treating is carried out at about 75° C. to about 100° C.

5. The process according to claim 1, wherein the hydrogenation catalyst is a heterogeneous catalyst.

6. The process according to claim 5, wherein the heterogeneous catalyst is a heterogeneous platinum group metal (PGM) catalyst.

7. The process according to claim 1, wherein the aqueous acidic solution of the compound of formula (3) comprises about 0.05 area % or less of the compound of formula (1) as determined by HPLC.

8. The process according to claim 1, further comprising treating the aqueous acidic solution of the compound of formula (3) to form solid a salt of compound (3).

9. The process according to claim 8, wherein the solid salt of the compound of formula (3) comprises about 0.05 area % or less of the compound of formula (1) as determined by HPLC.

10. The process according to claim 8, further comprising converting the solid salt of the compound of formula (3) to a free alkaloid of the compound of formula (3).

11. A The process according to claim 1, further comprising treating the aqueous acidic solution of the compound of formula (3) at about 45-50° C. with a base to form the alkaloid of the compound of formula (3).

12. The process according to claim 10, wherein the alkaloid of the compound of formula (3) comprises about 0.05 area % or less of the compound of formula (1) as determined by HPLC.

13. A process for preparing a compound of formula (3), comprising:
(I) hydrogenating an aqueous acidic solution comprising a compound of formula (1) and a compound of formula (2), wherein the hydrogenation is carried out at ambient temperature in the presence of a hydrogenation catalyst and hydrogen gas; and
(II) hydrogenating the product of step (I) at a temperature greater than ambient temperature in the presence of a hydrogenation catalyst and hydrogen gas to form an aqueous acidic solution of the compound of formula (3) comprising 0.05 area % or less of the compound of formula (1) as determined by HPLC and 2.00 area % or less of a compound of formula (4) as determined by HPLC,

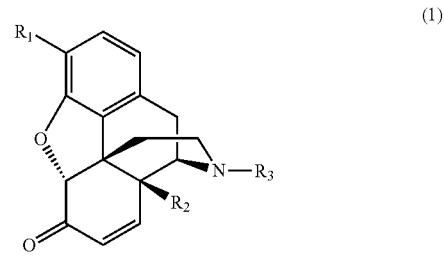

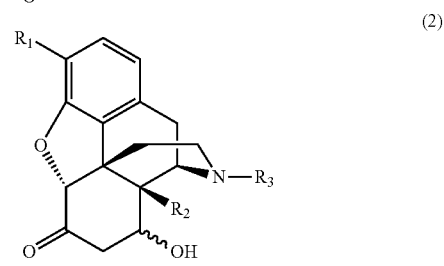

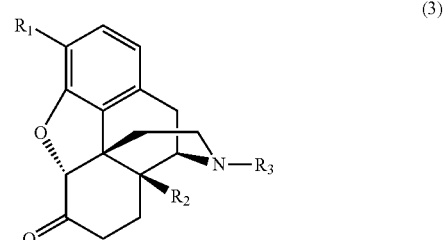

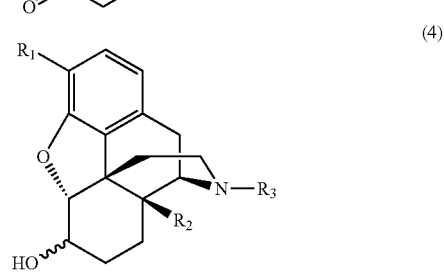

wherein:
i) $R_1$ is —OH, $R_2$ is —OH and $R_3$—H;
ii) $R_1$ is —OCH$_3$, $R_2$ is —H and $R_3$—CH$_3$;
iii) $R_1$ is —OH, $R_2$ is —H and $R_3$—CH$_3$;
iv) $R_1$ is —OCH$_3$, $R_2$ is —H and $R_3$—H;
v) $R_1$ is —OH, $R_2$ is —H and $R_3$—H; or
vi) $R_1$ is —OCH$_3$, $R_2$ is —OH and $R_3$—H.

14. The process according to claim 13, wherein $R_1$ is —OH, $R_2$ is —OH, and $R_3$—H.

15. The process according to claim 13, wherein the acid in the aqueous acidic solution is acetic acid, phosphoric acid, citric acid, tartaric acid, oxalic acid, hydrochloric acid, hydrobromic acid, or a mixture thereof.

16. The process according to claim 1, wherein the hydrogenation catalysts of step (I) and step (II) are, independently, a heterogeneous or homogenous catalyst.

17. The process according to claim 16, wherein the heterogeneous catalyst is a heterogeneous platinum group metal (PGM) catalyst.

18. The process according to claim 13, wherein the hydrogenation of step (II) is carried out at about 75° C. to about 100° C.

19. The process according to claim 13, further treating the aqueous acidic solution of the compound of formula (3) to form a solid salt of compound (3).

20. The process according to claim 19, wherein the solid salt of the compound of formula (3) comprises about 0.05 area % or less of the compound of formula (1) as determined by HPLC.

21. The process according to claim 19, further comprising converting the solid salt of the compound of formula (3) to a free alkaloid of formula (3).

22. The process according to claim 13, further comprising treating the aqueous acidic solution of the compound of formula (3) at 45-50° C. with a base to form the alkaloid of the compound of formula (3).

23. The process according to claim 21, wherein the alkaloid of the compound of formula (3) comprises about 0.05 area % or less of the compound of formula (1) as determined by HPLC.

24. The process according to claim 6, wherein the heterogeneous catalyst is a heterogeneous palladium catalyst.

25. The process according to claim 16, wherein the catalyst is a heterogeneous catalyst.

26. The process according to claim 17, wherein the PGM catalyst is a heterogeneous palladium catalyst.

\* \* \* \* \*